United States Patent [19]

Pohl

[11] 4,326,934

[45] Apr. 27, 1982

[54] CONTINUOUS DIELECTROPHORETIC CELL CLASSIFICATION METHOD

[76] Inventor: Herbert A. Pohl, 515 Harned Ave., Stillwater, Okla. 74074

[21] Appl. No.: 108,709

[22] Filed: Dec. 31, 1979

[51] Int. Cl.³ ............................................. B01D 57/02
[52] U.S. Cl. ................................................ 204/180 R
[58] Field of Search ............................ 204/186, 180 R

[56] References Cited

U.S. PATENT DOCUMENTS

| | | | |
|---|---|---|---|
| 3,162,592 | 12/1964 | Pohl | 204/186 |
| 3,930,982 | 1/1976 | Batta | 204/299 |
| 4,181,589 | 1/1980 | Frosch | 204/180 R |

OTHER PUBLICATIONS

Canadian J. of Microbiology, 17, pp. 879–888 (1971).
Quar. Rev. of Biophys., 8, pp.421–438 (1975).
Dielectrophoresis, Pohl, H. A., Cambridge University Press, 1978, pp. 432–440.

*Primary Examiner*—Howard S. Williams
*Attorney, Agent, or Firm*—Arnold, White & Durkee

[57] ABSTRACT

An apparatus and method for classifying, characterizing, or sorting neutral particles, cells or their parts are disclosed. The apparatus and method are based upon both the positive and negative dielectrophoretic movement of neutral particles, cells, microorganisms or organalles when subjected to a nonuniform electric field generated between two electrodes, the exterior surfaces of which are separated by not more than 900 microns. The apparatus and method are particularly applicable with low conductivity suspensions of living cells or their parts.

4 Claims, 10 Drawing Figures

FIG. 8 existed for an apparatus and method to classify large quantities of neutral particles in relatively short periods of time.

SUMMARY OF THE INVENTION

The apparatus and method of the present invention which involves applying nonuniform field effects in a continuous manner to a flowing suspension of cells overcome many of the disadvantages of the prior art.

The present invention provides an apparatus and method for classifying, i.e., sorting or characterizing, neutral particles, including cells, in a fluid based upon their electrical polarizabilities in a nonuniform electric field. Continuous dielectrophoresis may produce continuous separation of cells from mixtures of cells of different types or of different physiological states. Continuous dielectrophoresis can also be used to characterize cells of a single type according to their polarizability.

The discovery of the instant invention comprises an apparatus having a plurality of electrodes capable of producing a nonuniform electric field and separated in an isomotive field by having r60, as defined in the Detailed Description be not more than about one millimeter when used with aqueous suspensions. A particularly useful separation of the electrodes is about 900 microns at r60. In a non-isomotive nonuniform electric field the electrodes should not be closer than about one millimeter to the stream of cells to be separated. These electrodes are connected to an AC electrical source capable of producing a constant voltage over a wide range of frequencies.

The apparatus further comprises a dielectrophoresis conduit or channel through which the neutral particles or cells are flowed and in which dielectrophoresis takes place. This conduit is positioned between the electrodes and within the generated nonuniform electric field. The conduit is a free volume for flow of the approximately stream-centered flow of neutral particles or cells and support fluid. In the "wet-electrode" embodiment of the invention, the electrodes form one or more of the walls of the conduit. In the "dry-electrode" embodiment of the invention, the conduit is formed by a nonconducting material placed within the nonuniform electric field adjacent and in contact with the electrodes.

In some embodiments the electrodes themselves may form at least a part of the conduit. In other embodiments the conduit is made of a nonconductive material, such as lucite, and the conduit is placed between the electrodes. In some embodiments the conduit may be of such a size as to contact the electrodes.

The apparatus of the instant invention is used to classify neutral particles. The particles are flowed through the conduit where the nonuniform electric field dielectrophoretically deflects the particles. The magnitude of this deflection can be measured after the particles leave the field. A plot of this deflection versus frequency of the applied AC field characterizes the particles.

If the stream of particles were comprised of two or more types of particles, separation will occur and can be measured.

Stream-centered flow is preferred to minimize flow velocity differences near the walls of the conduit.

Another feature of the invention is a concentric injection system for the production and injection of an approximately stream-centered flow of cells in a supporting fluid.

Cell characterization may be accomplished by using this apparatus with a single cell type. To obtain a spectrum characteristic of a given type of cell, the frequency of the AC current is varied and the displacement of the cell stream from an initial reference point with no field applied, i.e. the effective dielectrophoretic force acting upon the cell, is measured and plotted against the frequency of the AC field.

This spectrum of dielectrophoretic displacement versus frequency of the applied AC field is useful in cell characterization. Further, it offers the ability to identify unknown pure cell types by comparison of an experimental spectrum with spectra of known cell types.

The same apparatus may be used for cell sorting of a mixture of cells by operating at a single optimum AC frequency to produce the optimal separation between the cells to be separated. When operated in a cell-sorting mode, the apparatus will separate different types of cells in an approximately stream-centered mixture comprising two or more cell types.

While the invention will be described in connection with the preferred embodiment, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE PREFERRED EMBODIMENT

The realization of the "isomotive" electrode configuration and of practically useful forces in aqueous media places restrictions upon the physical size and separation of the electrodes and on the size of the useful effective isomotive field region.

The time-averaged force $\vec{F}$ on a body of complex permittivity $\epsilon_2$ in a medium of complex permittivity $\epsilon_1$

CONTINUOUS DIELECTROPHORETIC CELL CLASSIFICATION METHOD

BACKGROUND OF THE INVENTION

The invention relates to the use of dielectrophoresis in neutral particle classification, i.e., characterization and sorting. More particularly, an apparatus and method to produce continuous separation of neutral particle mixtures by the use of dielectrophoresis is disclosed. Further, the apparatus and method are particularly useful for the classification, i.e., characterization and separation, of living cells and their parts.

The need exists for methods of characterizing cells and separating out pure populations of cells from mixtures of cells. Cells which exhibit different functions and stages of differentiation must be separated from one another to facilitate the study of some of the molecular mechanisms involved in cell specialization, cytotoxicity and transformation. Diagnosis of diseased states and use of isolated cells for immunotherapy or transfusion purposes are areas where practical benefits of cell separation techniques may be attainable. It is of importance, for example, in the characterization of basic processes of cell differentiation and regulation, or of abnormalities. Looking ahead, it is not difficult to foresee that cell separations may play a vital roll in the diagnosis and treatment of disease. The problems of cell separation have received considerable attention in the past, resulting in the development of numerous separation methods. The techniques of electrophoresis and sedimentation were recently reviewed by Mel and Ross. 8 Quartr. Rev. Biophys. 421 (1975). Mel and Ross discussed sedimentation-centrifugation and electrophoresis. Methods using spectrophotometric signals on streams of cells to evoke a later "electrostatic" deflection of the droplet containing the labeled cell have been devised and offer considerable promise. Arndt-Jovin and Jovin, 7 Ann. Rev. of Biophys. Bio-eng. 527 (1978); Owen, 22 Biophys. J. 171 (1978). Fluorescence-activated cell sorting has been described by van Dilla. 163 Science 1213 (1969). A particularly interesting technique using high gradient magnetic fields has been described by Molday and by Kronick. Molday, 268 Nature (London) 437 (1977); Kronick, 200 Science 1074 (1978).

Dielectrophoresis has been defined as the motion of a neutral particle due to the action of a nonuniform electric field on its permanent or induced dipole moment. When a particle is introduced into a system with a nonuniform electric field, the field induces a dipole in that particle. The divergent nonuniform nature of the field results in one end of the dipole being in a region of higher field strength than the other. The effect is that the dipole is pulled in the direction of the increasing field.

Nonuniform electric fields can induce translational and rotational motions of cells in suspension. These motions can be used to characterize and usefully separate living cells and their parts. The nonuniform field acts by aligning or inducing a dipole moment in the cell. The cell is then impelled by the field nonuniformity, usually towards the region of greatest field intensity.

The force created is known as the dielectrophoretic force, and the resulting motion dielectrophoresis. In the event the cell being acted upon is suspended in a polarizable medium, the net polarization of the whole may be such as to evoke a dielectrophoretic force in favor of pushing the body either into or away from the region of higher field intensity. The cell experiences "positive" dielectrophoresis when it is forced into the region of higher field intensity; "negative" dielectrophoresis results when the cell is pushed away from the region of higher field intensity.

It is well-known that a neutral particle, when subjected to the influence of a nonuniform, time varying (AC) electric field, may exhibit one of the following behaviors:
(1) Positive dielectrophoresis, i.e. attraction toward the region of high field intensity;
(2) Negative dielectrophoresis, i.e. repulsion toward the region of lower field intensity; or
(3) Zeresis, i.e. no net displacement.

These processes arise from the following sequence of phenomena. The electric field induces a charge separation or dipole in the neutral particle. The resultant dipole consisting of equal numbers of slightly separated positive and negative charges now experiences a net force upon it because of the nonuniformity of the electric field. One or the other of the charge sets will be in a weaker electric field. Since the force upon a charge is exactly dependent upon the amount of charge, and upon the local field acting upon that charge, it will be seen that a net force arises upon the particle, despite the fact that it is neutral overall and has no excess charge of either type. The same considerations apply to the supporting fluid medium. The net of these dielectrophoretic forces upon the particle and its supporting medium acts to impel the particle toward the stronger field in positive dielectrophoresis. If, on the other hand, the net force upon the particle and medium is such as to impel the particle toward the region of weaker field, negative dielectrophoresis results.

In electrophoresis, the field induced motion of charged particles, the direction of the force is dependent upon the sign of the charge and upon the direction of the field. However, in dielectrophoresis, the force depends upon the square of the field intensity, and is independent of the direction of the field. For this reason, dielectrophoresis works well in AC fields.

For a particle to experience either positive or negative dielectrophoresis it must be subject to a divergent electric field. In practice, nonuniform electric fields can be realized using any of many electrode geometries. Pohl, 5 J. Electrostatics 337 (1978) discussing these geometries is incorporated by reference herein. However, in order to obtain sharp cell separations, it is considered that the "isomotive" field is the most appropriate, as it offers a constancy of dielectrophoretic force operating over a relatively wide region. Theoretical considerations in the design of "isomotive" cell electrodes are discussed in U.S. Pat. No. 3,162,592, incorporated by reference herein.

Among the factors which must be given close attention during the successful separation of living cells by continuous dielectrophoresis are:
(1) avoidance of local overheating, as by the application of high local current in Joule Heating;
(2) minimization of dead-flow pockets;
(3) minimization of turbulence;
(4) avoidance of cell damage as by grinding, adhesion or heat, and by electrolytic or chemical changes, as of pH;
(5) maintenance of the individuality of cells.

The need existed in the prior art for an apparatus and method meeting the above factors. Further, the need placed in a nonuniform electric field originally of strength $\vec{E}_o$ is given by the expression $$\vec{F} = -(\tfrac{1}{4}) \int_{body}^{Re} \left( \nabla \left( \epsilon_1^* \left(1 - \frac{\epsilon_2}{\epsilon_1}\right) \vec{E}_o^* \cdot \vec{E} \right) \right) dv \quad (1)$$

The asterisk indicates the complex conjugate of the quantity starred, and $\vec{E}$ is the resultant field throughout the body. For a spherical body, this reduces to the simpler expression $$\vec{F} = 2\pi a^3 Re \left[ \epsilon_1^* \frac{(\epsilon_2 - \epsilon_1)}{(\epsilon_2 + 2\epsilon_1)} \right] \nabla(E_o)^2 \quad (2)$$

where a is the particle radius. The complex (frequency dependent) permittivity is given by $$\epsilon = \epsilon_o(K' - iK'') = \epsilon_o K' - i\sigma/\omega \quad (3)$$

where K' and K'' are the in-phase and out-of-phase relative dielectric constants, $\sigma$ is the conductivity, $\omega$ is the angular frequency of the applied field, and i is the square root of minus one.

The dielectric constant and the conductivity of real materials are "constants" of the materials only at a particular frequency, and reflect the slope of the polarization versus field strength relation at that frequency. Normally, the dielectric constants and conductivities are monotonically varying functions of the frequency. The interplay of these variations between the suspended body and the surrounding medium gives rise to a new polarization of the body in the medium which can have rather complicated shapes over the frequency range. The effective net polarization given by the quantity in brackets in Eq. 2 can have positive and negative values over the frequency range. It is this feature of the net polarization of real systems which gives rise to the complicated dielectrophoretic collection rate spectra. Where the net polarization of the system is negative, negative dielectrophoresis is to be expected upon the application of a nonuniform electric field.

In order to evaluate the probable magnitude of the dielectrophoretic force on a living cell, such as that of a single yeast cell, the values of the physically realizable parameters need to be known. For simplicity, the effective net polarizability is designated as $K_e$, where $$\epsilon_o K_e = Re \left[ \frac{\epsilon_1^* (\epsilon_2 - \epsilon_1)}{(\epsilon_2 + 2\epsilon_1)} \right] \quad (4)$$

and $\epsilon_o$ is the permittivity of free space, so that $$\vec{F}_e = 2\pi a^3 \epsilon_o K_e \nabla(E_o)^2 \quad (5)$$

For frequencies in the range of interest, values of $K_e$ range from zero to about 100 for single yeast cells.

Figure 9:
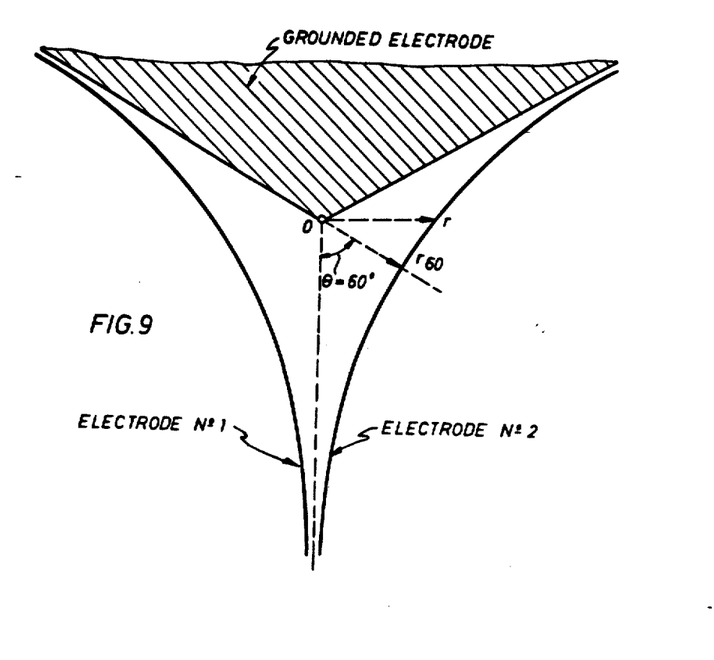
FIG. 9 illustrates the isomotive electrode configuration.
Figure 10:
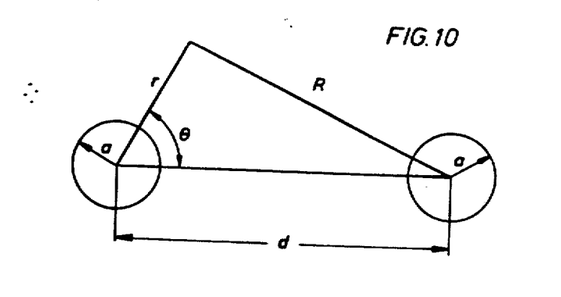
FIG. 10 illustrates the geometry of the wire-wire electrode system.

The practical magnitude for the field gradient term, $\nabla(E_o)^2$, should be evaluated for particles in an isomotive field, where the magnitude of the dielectrophoretic force, $|\vec{F}| = kr^o$, is independent of the position coordinate r, and all particles present are subject to identical forces, no matter what the position of the particle in the electrode confines (see FIG. 9). In practice, this ideal cannot quite be met for very large regions because of the limitations of geometry, and of practically useful field strengths which may be applied without excessive heat generation in conductive dielectrics such as the watery suspension of cells. The isomotive configuration can be approximated to a reasonable degree to obtain the benefits of having a practically uniform force operating over short regions.

The size of the practical region for the operation of nonuniform field forces on biological particles in aqueous media is a necessary datum for the successful application of dielectrophoresis to biological problems. In such applications, a biological particle such as a cell must be made to respond to the applied nonuniform field at a reasonable rate. A velocity at least of about 1.0 $\mu$m per second is usually required. Stoke's relation for the velocity of spherical particles can then be used to estimate the necessary gradient of the square of the applied nonuniform electric field.

$$\vec{F}_v = 6\pi \eta a \vec{v} \quad (6)$$

When the particle is moving in a steady state under the influence of the applied field, the dielectrophoretic and drag forces will be in balance, $$\vec{F}_d = \vec{F}_v \quad (7)$$

from which we find on equating Eqs. 2 and 6 that $$\nabla(E_o)^2 = \frac{3\eta v \hat{r}}{(a^2 \epsilon_o K_e)} \quad (8)$$

where $\hat{r}$ is the unit radial vector in the cylindrical geometry. Upon inserting reasonable values for the several parameters as known for yeast cells, for example, i.e., $a = 4$ $\mu$m s$^{-1}$, and $\eta = 0.010$ poise $= 0.0010$ Kg m$^{-1}$s$^{-1}$ for the viscosity of water, we can calculate that a conditional value of the necessary gradient magnitude is $$|\nabla(E_o)^2| = 2.12 \times 10^{11} V^2 m^{-3}. \quad (9)$$

If we have isomotive field conditions, the dielectrophoretic force is constant along a radial direction and the above value of $|\nabla(\vec{E} \cdot \vec{E})|$ can be used to evaluate the electrode dimensions.

The field in the charge-free region between the electrodes shown in the diagram of FIG. 9 is described by the Laplace equation for the potential, V, $\nabla^2 V = 0$ (10) subject to the boundary condition that the force on the small spherical body, $\vec{F}_e$, is constant in a given radial direction. Eq. 5 for simplicity is rewritten as $$\vec{F}_e = 2\pi a^3 \epsilon_o K_e \nabla(E_0)^2 = F_r(r^o)\hat{r} \quad (5')$$

where $F_r(r^o)$ is a constant along the radial coordinate. The solution of the Laplacian in cylindrical coordinates, assuming constancy of the potential surfaces in the z-direction is $$V = Ar^n \sin(n\theta) \quad (11)$$

which yields $\vec{E}_0 = -nAr^{n-1}(\hat{r}\sin(n\theta) + \hat{\theta}\cos(n\theta)) \quad (12)$ and $E_o^2 = n^2 A^2 r^{2n-2} \quad (13)$ and $\nabla(E_o)^2 = 2(n-1)n^2 A^2 r^{2n-3}\hat{r} \quad (14)$ For the force to be independent of the radial coordinate, this requires that $n=3/2$, so $$\nabla(\vec{E} \cdot \vec{E}) = 9A^2\hat{r}/4 \qquad (15)$$

$$V = Ar^{3/2}\sin(n\theta) = A(r_{60})^{3/2}; \qquad (16)$$

accordingly,
where $r_{60}$ is the value of the radial distance coordinate at $\theta=60°$, hence $$r^{3/2} = (r_{60})^{3/2}\left(\sin\left(\frac{3}{2}\theta\right)\right)^{-1} \qquad (17)$$

and $A = V(r_{60})^{-3/2}$ \qquad (18)

$$\text{so } \nabla(\vec{E} \cdot \vec{E}) = \frac{9}{4}V^2\hat{r}(r_{60})^{-3} \qquad (19)$$

Combining this with Eq. 10, yields $$F_r = \frac{9}{2}\pi a^3 V^2 (r_{60})^{-3}\epsilon_o K_e \qquad (20)$$

$$\text{or } F_r = \frac{9}{2}a^3V^2(r_{60})^{-3}Re\left\{\frac{\epsilon_1^*(\epsilon_2 - \epsilon_1)}{\epsilon_2 + 2\epsilon_1}\right\} \qquad (21)$$

Inserting the conditional value for the gradient obtained earlier (following Eq. 8), and assuming an impressed voltage of 10 volts across the electrode pair, as is reasonable for use in aqueous media, yields from Eq. 19 that the value for $r_{60}$ is $$r_{60} = \left[\frac{9V^2}{\nabla(\vec{E} \cdot \vec{E})}\right]^{\frac{1}{3}} = \left[\frac{9 \times 10 \times 10}{4 \times 2.12 \times 10^{11}}\right]^{\frac{1}{3}} = 1.02\text{mm}; \qquad (22)$$

This small value of the required dimensions, about one millimeter for the critical spacing of electrodes in dielectrophoresis chambers to be applied to aqueous suspensions is quite restrictive. It places a limit on the size of the regions in which one can expect to maintain reasonable control over suspended biological material. Accordingly, this consideration must be followed in the construction and use of operable dielectrophoretic systems for biological particles.

With an impressed voltage of ten volts across the electrode pair, a reasonable value for use in aqueous media, the electrode spacing is restricted to having $r_{60}$ being no greater than approximately one millimeter. This small value of the required dimensions, about one millimeter for the critical spacing of electrodes in dielectrophoresis chambers to be applied to aqueous suspensions is quite restrictive. It places a limit on the size of the regions in which one can expect to maintain reasonable control over biological material suspended in aqueous media.

For an ideal isomotive situation, the gradient of the square of the externally applied AC field should remain constant throughout the cross-section of the dielectrophoresis conduit. The "dry electrode" configurations shown in FIGS. 1–2, produce a field distribution closely simulating the ideal isomotive situation for a reasonable region inside the conduit, the gradient remaining reasonably constant over a fairly wide region, i.e. 350 to 850 microns within the conduit.

Figure 1:
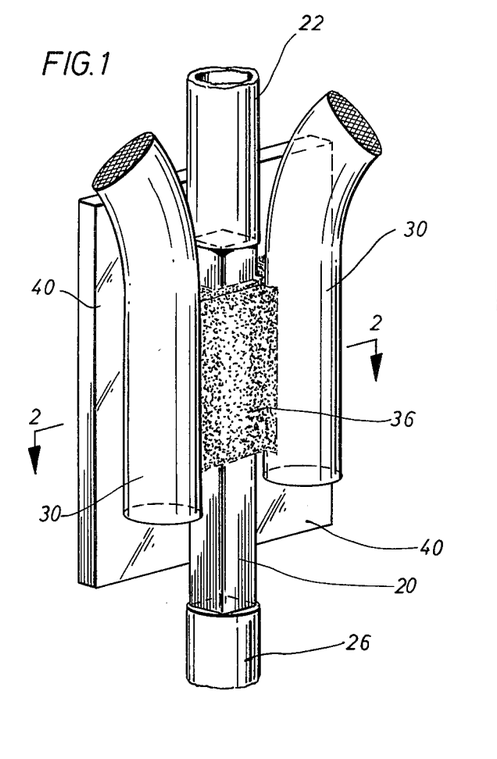
FIG. 1 is a drawing of a "dry electrode" embodiment of the dielectrophoresis chamber described by the present invention. It illustrates the dielectrophoresis chamber and parallel electrodes.
Figure 2:
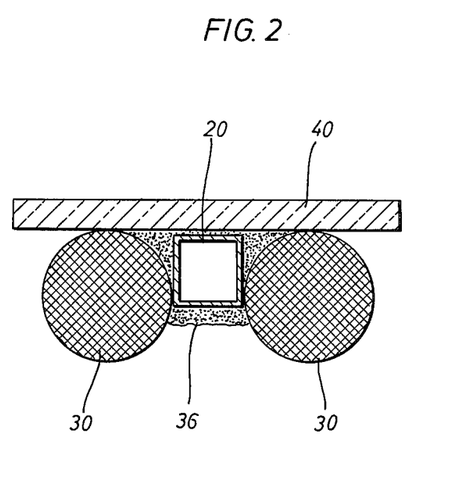
FIG. 2 is a cross-sectional view of the dielectrophoresis chamber illustrated in FIG. 1.

FIGS. 1 and 2 illustrate an embodiment of a dielectrophoresis cell described by the present invention. This embodiment is the "dry electrode" embodiment. The continuous flow dielectrophoresis cell comprises a conduit mounted on a microscope slide 40. The conduit must be of such size and configuration so as to fit between the two electrodes used to produce the nonuniform electric field. The conduit may be approximately 10 to 50 millimeters in length. Neutral particles or cells to be classified may enter the conduit 20 through connector 22. After passing through conduit 20 and being acted upon by the nonuniform electric field, the particles or cells exit through connector 26. Two electrodes 30 the exterior surfaces of which are separated by no more than about one millimeter at $r_{60}$, may be placed parallel and adjacent to either side of the dielectrophoresis conduit 20 to generate the nonuniform electric field. Other electrode configurations are also acceptable so long as their exterior surfaces are separated by having $r_{60}$ being no more than about one millimeter. The dielectrophoresis conduit 20 and electrodes 30 may be secured with a non-conducting adhesive such as an epoxy polymer 36 on a glass microscope slide 40 to form the dielectrophoresis chamber.

Figure 3:
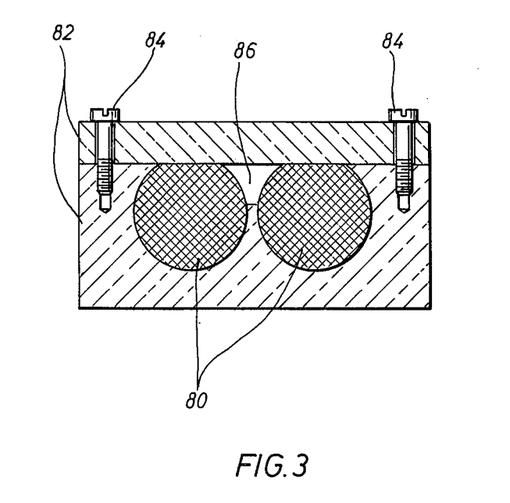
FIG. 3 illustrates a cross-sectional view of the preferred embodiment of the invention. This is a "wet electrode" embodiment.

FIG. 3 illustrates a cross-section of the preferred embodiment of a dielectrophoresis cell described by the present invention. The preferred embodiment is a "wet electrode" embodiment. The continuous flow dielectrophoresis cell comprises a pair of parallel electrodes 80 having isomotive shape and whose exterior surfaces are separated by having $r_{60}$ being not more than about one millimeter. These electrodes are rigidly held in insulating material 82, such as Lucite or Plexiglas, by fastening means such as screws 84. A conduit 86 is formed in the free space between electrodes 80 and insulators 82. Neutral particles or cells to be classified flow through conduit 86 and are acted upon by the nonuniform electric field in the preferred embodiment in the same manner as described above for the "dry electrode" embodiment.

Figure 4:
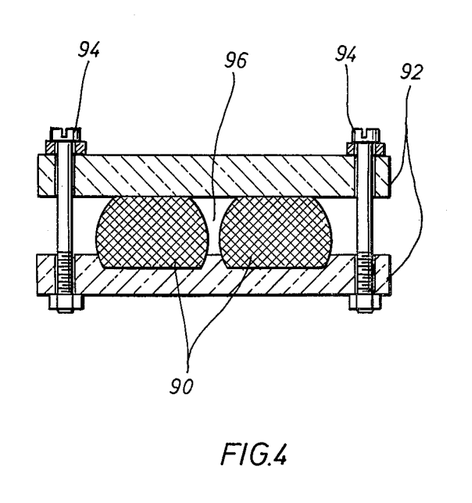
FIG. 4 illustrates a cross-sectional view of another embodiment of the "wet electrode" configuration of the invention.

FIG. 4 illustrates a cross-section of another "wet electrode" embodiment. The continuous flow dielectrophoresis cell comprises a pair of parallel electrodes 90 having isomotive shape and whose exterior surfaces are separated by not more than about one millimeter at $r_{60}$. These electrodes are rigidly held in insulating material 92, such as Lucite or Plexiglas, by lasting means such as screws 94. A conduit 96 is formed in the free space between electrodes 90 and insulators 92. Neutral particles or cells to be classified flow through conduit 96 and are acted upon by the nonuniform electric field in the same manner as in the "dry electrode" embodiment described above.

Figure 5:
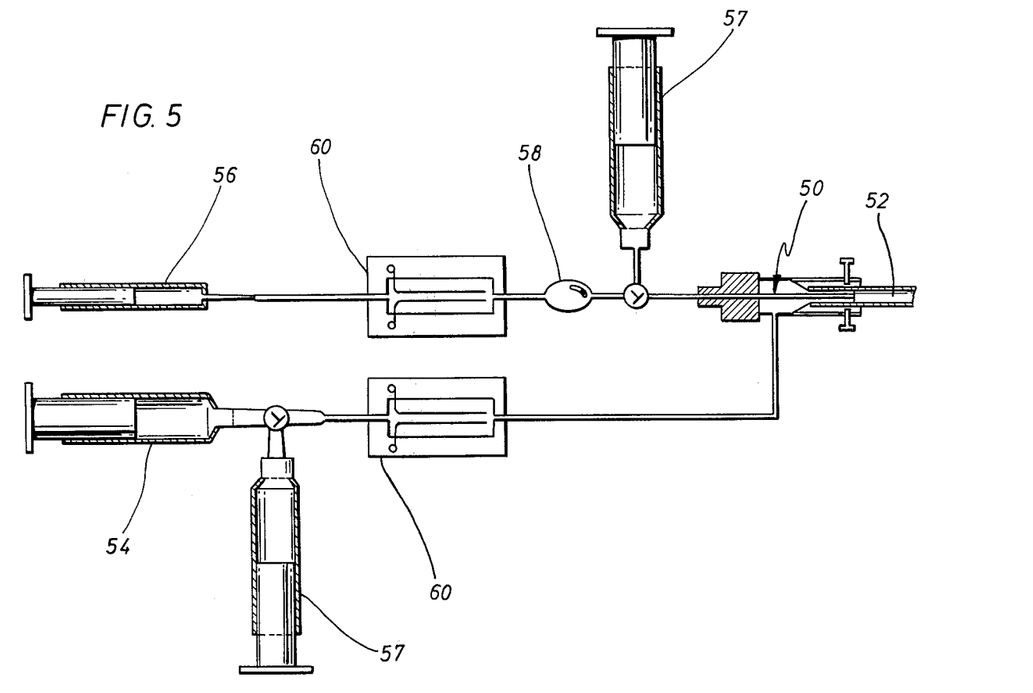
FIG. 5 illustrates a cell injection system to produce a stream-centered flow of cells in a continuous dielectrophoresis classification apparatus.

FIG. 5 illustrates an apparatus which may be used to produce a continuous stream-centered flow of cells within a supporting medium. An injector comprising a concentric arrangement of a small needle, 50, such as #31 gauge 0.25 millimeter outside diameter, 0.13 millimeter inside diameter gas chromatograph needle, centered within a larger needle 52, such as a #20 gauge 0.58 millimeter inside diameter hypodermic needle is illustrated as a means of injecting a concentrated cell suspension into the center of a supporting fluid stream to provide an approximately stream-centered flow of cells. This arrangement produces a narrow stream of cells approximately in the center of the dielectrophoresis conduit. The diameter of the central cell stream produced with this injection system is typically on the order of 10 to 100 microns in a dielectrophoresis conduit of 900 microns inside diameter. Any injection system providing a continuous stream centered flow of cells may be employed. A representation of an injection system is shown in FIG. 3. The two liquids may be supplied from syringes mounted in an infusion pump. The support stream may be supplied from a 5 milliliter syringe 54 at a flow rate of $9.6 \times 10^{-3}$ milliliters per minute. The cell suspension may be injected from a 50 microliter syringe 56. This apparatus propells the cells through the dielectrophoresis conduit at an average velocity of approximately 200 microns per second. At this velocity the cells are subjected to the nonuniform field for approximately 100 seconds in the preferred embodiment. Other residence times will be observed for different flow velocities and conduit lengths. Syringes 57 provide means to refill the support stream syringe 54 and the cell suspension syringe 56.

The smaller, cell suspension stream may also contain an in-line glass supply chamber 58 of about 1 milliliter of volume containing a magnetic stirrer to maintain the cells in suspension during the course of classification.

Conductivity cells 60 may be incorporated to measure the conductivity of each stream. It is important to insure that both streams have the same conductivity so as to minimize bulk polarization effects masking the polarization of the cells. Conductivity should be kept below $10^{-3}$ mhos/cm and preferably below $10^{-5}$ mhos/cm so as to minimize thermal effects. The conductivity may be adjusted with KCl solutions.

The support fluid is most often water, although any low conductivity fluid, such as liquid fluorocarbons may be used. When working with living cells the support fluid should be non-toxic. An iso-osmotic fluid should be used when working with cells without walls.

Figure 6:
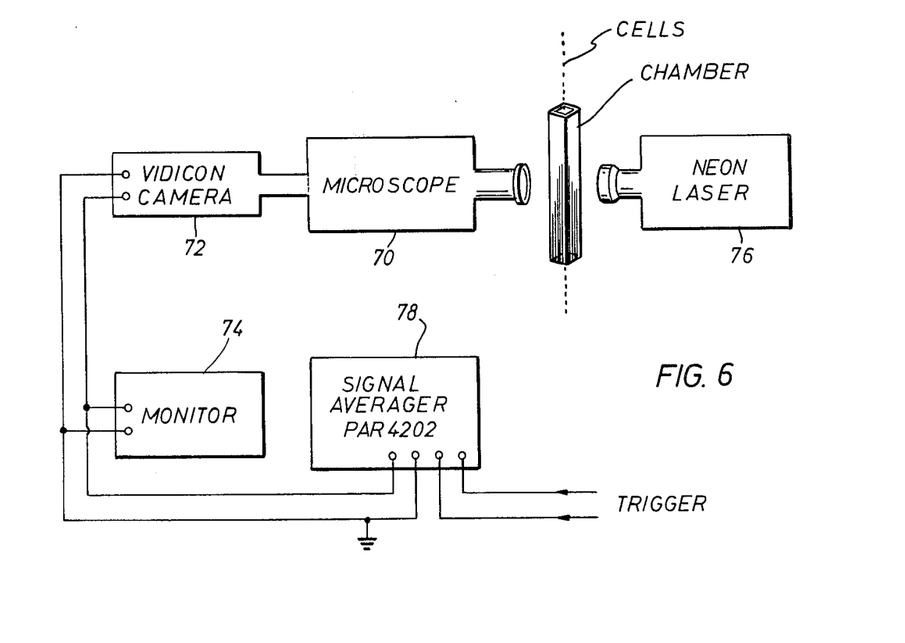
FIG. 6 is a schematic illustration of a monitoring and recording system which may be used with the present invention.

FIG. 6 schematically illustrates a system which may be used to view the cell classification. The dielectrophoresis chamber may be mounted on a microscope stage for observation. A microscope 70 may be set on its back so that the chamber is held vertically upright. A vidicon camera 72 may be used to display the chamber contents on a monitor 74. The chamber may be illuminated at an anble by a neon laser 76 to provide dark field illumination. The video output may be fed through a signal averager 78 used in the multichannel scaling (MCS) mode and triggered by a 1.5 volt 60 Hz signal. The signal averager in the MCS mode allows a threshold voltage to be set so that only the voltage peaks of the illustrated cells are counted and registered while the background noise is filtered out. A dual memory signal averager enables a comparison of the position of the deflected stream to be made with respect to the undeflected stream.

When operated as a neutral particle or cell sorter, a flow of the mixture to be sorted is established in the dielectrophoresis conduit. A single AC voltage at the selected optimum frequency to provide the greatest neutral particle or cell separation is supplied across the electrodes for a time sufficient to produce this separation, following which time the spatial position of the different types of neutral particles or cells making up the central stream is recorded.

When operated in the neutral particle or cell characterization mode, a flow consisting of a single cell type is established. A known AC voltage at a selected frequency is applied across the electrodes for a time sufficient to produce maximum displacement of the cell stream, following which time the spatial position of the cells making up the central stream is recorded. This process is repeated at several different frequencies to produce a plot of frequency versus position (dielectrophoretic force) characteristic of the given cell type.

The invention will now be illustrated with two examples. The first example illustrates the use of the invention as a cell-sorter. The second example illustrates its use as a cell characterizer. The following experimental apparatus was employed in both examples.

A dielectrophoresis chamber of the "dry electrode" embodiment similar to that shown in FIG. 1 was constructed using a square capillary Microcell (Vitro Dynamics, Inc.) with a 900 micron inside diameter as conduit 20. Two cylindrical copper electrodes, two millimeters in diameter, were placed parallel to and adjacent either side of the conduit as shown in FIGS. 1 and 2 to provide the nonuniform field. The Microcell and electrodes were mounted to a glass microscope slide using a nonconducting epoxy polymer.

Voltages (50 to 150 volts rms at 10 KHz 232 MHz) were supplied across the dielectrophoresis chamber with a Hewlett-Packard 200CD audio oscillator and a Krohn-Heite model DCA wide-band amplifier. The voltages were measured with a Hewlett-Packard 410B volt meter.

The stream-centered cell injection system illustrated in FIG. 3 and described above was employed. Supply syringes 54 and 56 were mounted in a Harvard Apparatus model 975 infusion pump. The support stream was supplied at a rate of $9.6 \times 10^{-3}$ ml/min. The average cell velocity through the dielectrophoresis conduit was approximately 200 microns per second. The cells were subjected to the nonuniform electric field for approximately 100 seconds.

In line conductivity cells consisting of a flow chamber containing two parallel platinum blacked wires 2.5 centimeters long and 0.25 millimeters in diameter, as illustrated in FIG. 3, monitored the conductivity of each stream. Conductivity measurements were made using a General Radio 1650A impedance bridge at 1 KHz. In addition to the in line conductivity cells, a Yellow Springs Instruments 3403 dipping-type electrode was used as an occasional check on the inline cells. Conductivities were adjusted with KCl to maintain the same conductivity in each stream.

The dielectrophoresis chamber was mounted on a microscope stage for observation. The microscope (Bausch and Lomb model PB152) was set on its back so that the chamber was held vertically upright. An RCA model TC 1000 vidicon camera was used to display the chamber contents on a Harco NV-10A monitor. The conduit was eliminated at right angles to the side by a 2 mW Metrologic Laser focused by a 20 cm focal length lens to provide a dark field illumination.

The video output was fed to a PAR 4202 signal averager used in the multi-channel scaling (MCS) mode and triggered by a 1.5 volt 60 Hz signal. The signal averager in the MCS mode allowed a threshold voltage to be set so that only the voltage peaks of the illuminated cells were counted and registered while the background noise was filtered out. Two memories were available in the signal averager. A dual memory stored enabled a comparison of the position of the deflected stream to be made with respect to the undeflected stream.

EXAMPLE 1

A mixture contain the alga *Ankistrodesmus Falcatus* and the alga *Staurastrum Gracile* was prepared. The algae had been grow in aerated magnetically stirred 4-L aspirator bottles on Chu No. 10 culture medium. The preparation consisted of the repeated washing of each cell type using gentle centrifugation, washing off the cake, and resuspending the cells repeated with deionized water (resistivity, 500 Kohms-cm) until the desired conductivity was attained. The final suspension of each pure culture was then prepared by resuspending the cells in water of known conductivity containing KC1. The conductivity of the cell suspensions and of the support liquid would determined using a General Radio Model 1650 impedance bridge at 1 kHz, and platinum blacked electrodes in calibrated conductivity cells of known conductivity constant. The appropriate cell mixtures and the separate support liquid were then loaded into pumping syringes and a steady laminar flow was established in the dielectrophoresis chamber.

Once the central stream had been established in the chamber, a known AC voltage at the selected frequency was applied across the electrodes for a period of 180 second, following which time the spatial position of the two different types of cells making up the central stream was recorded. The above procedure was repeated for a range of frequencies (0.01–32 MHz) and voltage (30–150 Vrms).

Figure 7:
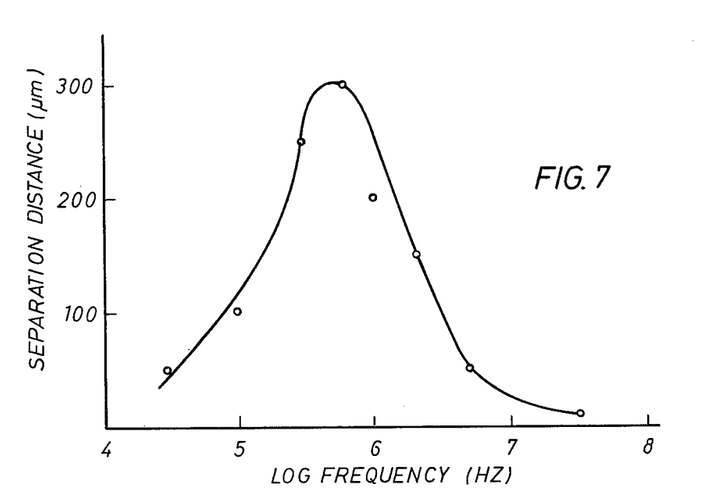
FIG. 7 illustrates the resulting separation of the alga Ankistrodesmus and the alga Staurastrum obtained when using the invention as a cell sorter.

With the *Ankistrodesmus-Staurastrum* mixture at 500 Kohms-cm, the two cell types could be readily separated by as much as 300 microns at an applied frequency of 600 kHz and an applied voltage of 60 Vrms. Control over the cells was virtually complete in that the use of the higher voltages available could cause the cells to be pulled against the wall of the capillary and, thus, move only very slowly. FIG. 7 illustrates the separation distance attained at various frequencies of applied AC field.

Additional separations are reported in Pohl, and Kaler, 1 cell Biophys. 15 (1979).

EXAMPLE 2

Figure 8:
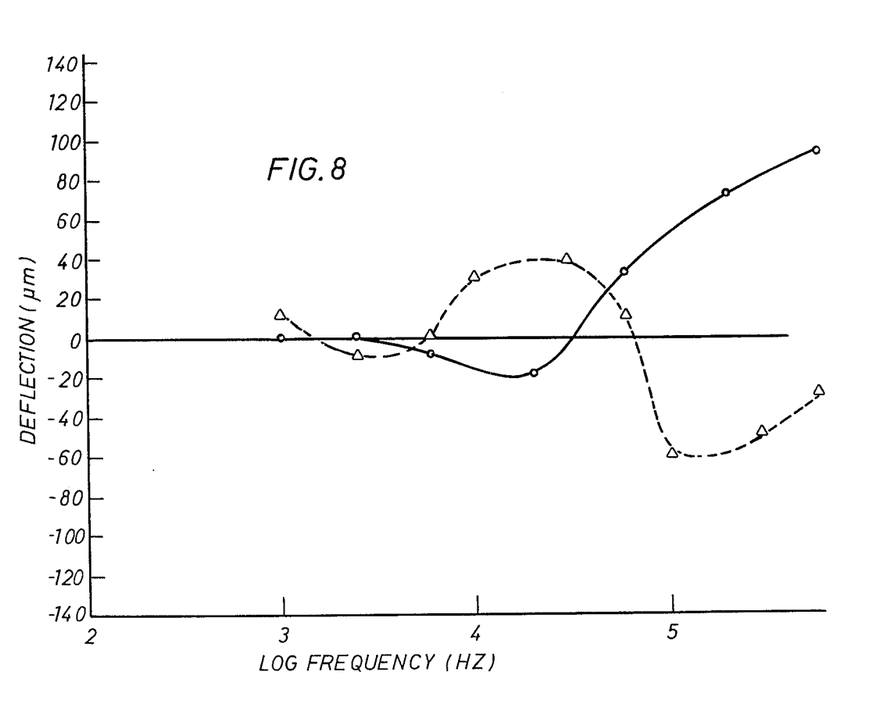
FIG. 8 illustrates characteristic spectra of the alga Chlorella Vulgaris at two different resistivities obtained when using the invention as a cell characterizer.

A cell characterization spectrum was obtained using the above experimental apparatus. An alga, *Chlorella Vulgaris*, was grown and prepared as in Example 1 above. A characterization spectrum was obtained at two different resistivities by varying the frequency of the applied AC field and recording the resulting deflections as provided in the method of the invention. FIG. 8 illustrates the resulting spectrum. In FIG. 8 the spectra defined by Δ----Δ was obtained in a solution whose resistivity was 13 Kohm-cm at an applied voltage of 100 Vrms. The spectrum illustrated in FIG. 8 by ⊙——⊙ was obtained in a support fluid of resistivity 130 Kohm-cm at an applied voltage of 50 Vrms.

The foregoing description of the invention has been directed in primary part to a particular preferred embodiment in accordance with the requirements of the patent statutes and for purposes of explanation and illustration. It will be apparent, however, to those skilled in the art that many modifications and changes in this specific apparatus may be made without departing from the scope and spirit of the invention. For example, other electrode configurations, such as three electrode configurations within the $r_{60}$ restrictions could be used to produce the nonuniform electric field, other conduit shapes and lengths could be used, or other flow rates or patterns employed.

It is applicant's intention in the following claims to cover such modifications and variations as fall within the true spirit and scope of the invention.

What is claimed is:

1. A method of classifying neutral biological particles based on the electrical polarization of said particles comprising,
   generating a non-uniform electric field between a plurality of approximately isomotive electrodes in which $r_{60}$ is not greater than about one millimeter, and
   exposing a stream of said particles in a biologically non-toxic fluid medium to said non-uniform electric field by passing said stream of particles between said electrodes.

2. A method as recited in claim 1, wherein said neutral particles are approximately stream-centered in a non-conducting fluid medium.

3. A method as recited in claim 1, wherein a mixture of said neutral particles having different electrical polarizabilities is separated into its component parts.

4. A method as recited in claim 1, wherein homogeneous neutral particles are characterized by production of a spectrum, further comprising,
   sequentially measuring the displacement of said stream of particles from an initial reference point in the absence of an electric field to its position in a non-uniform electric field generated at a plurality of frequencies by an alternated current power source.

* * * * *

UNITED STATES PATENT AND TRADEMARK OFFICE
CERTIFICATE OF CORRECTION

PATENT NO. : 4,326,934
DATED : April 27, 1982
INVENTOR(S) : Herbert A. Pohl

It is certified that error appears in the above-identified patent and that said Letters Patent is hereby corrected as shown below:

After sheet 3 of the drawings, sheet 4 as per attached page should be inserted.

Signed and Sealed this

Sixteenth Day of November 1982

[SEAL]

Attest:

Attesting Officer

GERALD J MOSSINGHOFF

Commissioner of Patents and Trademarks

FIG.9

FIG.10